United States Patent [19]
Garrison et al.

[11] Patent Number: 5,422,273
[45] Date of Patent: Jun. 6, 1995

[54] CELL COLLECTION APPARATUS

[75] Inventors: Donald L. Garrison, Salt Lake City; Larry E. Page, Sandy; Ronald S. Merrell, Provo, all of Utah

[73] Assignee: Baal Medical Products, Inc., Sandy, Utah

[21] Appl. No.: 36,180

[22] Filed: Mar. 23, 1993

[51] Int. Cl.$^6$ .......................... C12M 1/24; C12M 1/26
[52] U.S. Cl. ..................................... 435/296; 435/292; 422/102; 422/104; 128/756
[58] Field of Search ................ 128/756, 757, 759, 749, 128/750; 206/438, 828, 209, 209.1, 219, 361, 362.2, 362.3, 15.2, 15.3, 363; 215/DIG. 3; 435/292, 294, 295, 296, 312, 809, 810, 316; 422/99, 102, 104; 211/72, 73; 248/311.2

[56] References Cited

U.S. PATENT DOCUMENTS

| | | | |
|---|---|---|---|
| 3,062,380 | 11/1962 | Grela et al. | 211/73 |
| 3,518,164 | 6/1970 | Andelin et al. | 435/296 |
| 3,847,277 | 11/1974 | Doner | 211/73 |
| 3,881,464 | 5/1975 | Levene | 128/756 |
| 3,918,920 | 11/1975 | Barber | 422/104 |
| 4,273,416 | 6/1981 | Blum | 211/73 |
| 4,657,869 | 4/1987 | Richards et al. | 435/292 |
| 5,191,899 | 3/1993 | Strickland et al. | 128/756 |
| 5,226,744 | 7/1993 | Kemmerer | 401/4 |

FOREIGN PATENT DOCUMENTS

| | | | |
|---|---|---|---|
| 2554241 | 5/1985 | France | 435/296 |

OTHER PUBLICATIONS

Fisher Scientific Catalog (1986) p. 172.
Product Brochure from *Bibby Sterilin*, Staffordshire England, (no date supplied).
Product brochure from MICROVASIVE (no date supplied).

*Primary Examiner*—William H. Beisner
*Attorney, Agent, or Firm*—Workman Nydegger & Seeley

[57] ABSTRACT

An apparatus for use in the efficient collection of cell samples from a cytology brush device. The device is a cylindrical container capable of containing a solution. The open end is sealable with a removable cap. The closed end of the container is formed as a conically shaped end and disposed within the conically shaped closed end is a series of fins. The fins are oriented so as to form a fin passageway, which is capable of receiving the bristled portion of a cytology brush. When the cytology brush is rotated, the bristles are agitated against the fins, thus dislodging cell samples. The cell samples are then dispersed within the solution and later retrieved. Disposed at the open end of the container is an insert. The insert has an alignment opening which acts to keep the trailing end of the cytology brush aligned with the leading bristled end of the brush, as it is being rotated within the fin passageway. While the cytology brush device is rotated within the cylindrical container, the container is securely held to a support surface with a Z-shaped clamp. The clamp is attached to a support surface with an adhesive.

54 Claims, 6 Drawing Sheets

CELL COLLECTION APPARATUS

BACKGROUND

1. Field of the Invention

The present invention relates generally to an apparatus for use in the collection of cell samples from a cytology brush. More particularly, the present invention provides a cell collection apparatus which utilizes a unique combination of fins for agitating the bristles of a cytology brush within a fixative solution, thereby permitting the efficient and complete retrieval of the cell sample from the cytology brush.

2. Background Art

Detection and diagnosis of a variety of diseases, such as cancer, often involves the collection and microscopic examination of a cell sample. Typically, as with the Papanicolaou ("Pap") test, these cell samples are collected from a patient with a type of cytology brush device. After collection, the cell samples must be transferred from the bristles of the brush to some medium that allows for the examination of the cells.

Due to the typically serious nature of the disease that the doctor is attempting to detect, it is critical that the cell samples are completely and accurately transferred from the cytology brush to tile testing medium. Inaccurate retrieval of the cells can result in an inaccurate or delayed diagnosis of any underlying condition. Worse yet, inaccurate or incomplete retrieval of the cell sample could possibly result in the misdiagnosis of a serious medical condition.

Further, as is the case with the Pap smear, many women who have had an inadequate sample taken are reluctant to have the procedure repeated and may be placed at risk for progression of their disease until their next periodic checkup. A delay in the diagnosis of, for instance, cervical or uterine cancer can result in the need for far more radical treatment procedures than would be needed if the cancer were detected earlier. In the worse case, a delay in diagnosis could result in the progression from treatable cancer to a terminal cancer. Thus, a high yield of cells from only one attempt is important.

There are several problems that are encountered when cells are obtained from a cytology brush for later examination using current state of the art procedures. As is typically done after cells have been collected, they are transferred to a microscopic slide for later examination. This is accomplished by wiping the bristles of the cytology brush device directly against the smooth surface of the slide. A fixative is then applied to avoid any deterioration of the cells before the cytology technician and/or pathologist can examine them. However, it is very difficult to transfer all or even a large portion of the cells to a slide by merely wiping the bristles against the smooth slide surface. Thus, valuable diagnostic material is potentially lost. Again, this can increase the risk of an erroneous diagnosis.

This difficulty in transferring the cell sample to a slide is often made worse by the shape or type of cytology brush that is being used. For instance, a spiral shaped cytology brush is commonly used for a variety of cell collection procedures. Due to the shape of the brush, the cells can be transferred to the slide only by wiping, rubbing or rotating the brush against the slide surface. To transfer even a portion of the cells from this type of brush takes excess time and care. Thus, insufficient cell transfer can be very common when this type of brush and cell transfer method is used. Similarly, where a non-spiral type brush device is used, wiping can, at best, remove only a portion of the sample.

In some cases, the presence of mucous or blood or the knowledge that the patient is at high risk, can make the above type of slide preparation inappropriate. In that case, a monocellular preparation may be requested. In this technique, the samples must be transferred from the cytology brush device into a container of a fixative or other similar solution. The container is then centrifuged until all cellular components have: collected at the bottom of the container as a "cell pellet." After the excess fixative is pipetted off, the cell pellet can be spread evenly onto a slide. This provides a slide with very little cellular overlap. Mucous will have gone into solution and any red blood cells will be sufficiently spread so as to avoid obscuring other cells.

However, in this technique, the accuracy of the resulting "cell pellet" is again dependent on the successful and complete transfer of the cell samples disposed on the bristles to the fixative solution within the container. Typically, this transfer is done by placing the bristled end of the cytology brush within the centrifuge tube. The brush is then twirled within the fixative solution contained within the tube, in an attempt to dislodge all of the cells from the bristles. However, the twirling action within the fixative solution alone is often insufficient to dislodge all of the cells that are contained on the brush bristles. This is especially so with a spiral shaped brush, where it is difficult to sufficiently move the bristles within the fixative solution quickly enough so as to dislodge all of the cells. Again, the drawback is that often all of the cell samples are not transferred to the fixative solution, resulting in the same problems discussed above.

In addition, it is often difficult for the technician to hold the collection tube containing the fixative solution, and at the same time, sufficiently move the cytology brush bristles within the solution. To do so, the technician must attempt to hold the collection tube with one hand, and hold the cytology brush with the other, and then twirl, or otherwise move, the brush bristles within the solution so as to dislodge all of the cell samples. This can be awkward, and the potential of spilling and/or contaminating the cell sample and fixative solution is high.

BRIEF SUMMARY AND OBJECTS OF THE INVENTION

In view of the present state of the art, it is an object of the present invention to provide a cell collection apparatus that efficiently removes any cell samples that are disposed on the bristles of a cytology brush device and transfers them to a solution contained within the apparatus.

Another object of the present invention is to provide a cell collection apparatus that keeps a cytology brush stable and aligned while the cytology brush is being agitated within the cell removal means that is disposed within the apparatus.

It is a related object of the present invention to provide a cell collection apparatus that is able to accommodate cytology brush devices having different shapes and dimensions.

Yet another object of the present invention is to provide a cell collection apparatus that holds the collection apparatus in a rigid and stationary position while the cytology brush device is being rotated within the apparatus.

Additional objects and advantages of the invention will be set forth in the description which follows, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention is directed to an apparatus which provides for the easy and complete removal of cell samples disposed on the bristles of a cytology brush device. Accordingly, the apparatus is an elongate cylindrical container that has an open end and a closed end. Contained within the container is an appropriate collection solution, such as a standard fixative solution. The open end of the container can be closed with a screw-on cap, which seals the container in a liquid tight manner.

In one important aspect of the invention, the interior of the container at the closed end is formed into a conical shape. This allows for the easy formation of a cell pellet, or concentration of cell material, when the container is centrifuged. The conically shaped end also permits for the easy retrieval of the cell pellet with a pipette-type device.

In another important aspect of the invention, there is formed within the conically shaped portion of the container a series of fins. Each fin projects inwardly in an opposed but spaced apart relationship, and together they form a fin passageway. The leading end, or bristled portion of a cytology brush device can then be inserted within the container so as to be disposed within this fin passageway. As the cytology brush is then rotated, the bristles are rubbed against, and agitated by, the lateral edge of each of the fins. In this way, any cells that are present on the brush bristles are dislodged and thus suspended within the fixative solution.

In another important aspect of the invention, there is disposed at the open end of the cylindrical container a cylindrically shaped insert that is slidingly received within the open end of the container, and held there in a friction-tight manner. Fashioned through this insert is an alignment aperture. It is through this alignment aperture that the cytology brush device is inserted into the cylindrical container. The alignment aperture is shaped so that different types of cytology brush devices may be inserted through it, including spiral shaped brushes and brushes with laterally extending members. Additionally, the insert is also shaped so as to provide for the easy and unobstructed insertion of the leading edge of the cytology brush device.

The alignment aperture is also positioned so that it is aligned with the fin passageway located at the conically shaped closed end. Thus, when the leading bristled end of the brush is disposed within the fin passageway, the trailing handle end of the cytology brush is held by the alignment aperture in the same longitudinal alignment. This forced alignment of the cytology brush helps ensure that the leading end of the cytology brush stays disposed within the fin passageway as the cytology brush is being rotated.

In yet another important aspect of the invention, the cell collection apparatus also includes a holding device, or clamp. This clamp allows for the cylindrical container to be rigidly held to a support surface. The clamp is generally Z-shaped and is formed as a single integral piece from a resilient material. The clamp has two planar members that are formed at an angle to each other and each of which has a hole fashioned in it. The holes are of such diameter as to be capable of receiving the cylindrical container. The holes are placed in a substantially aligned position by compressing the two planar members together, at which time the container can be inserted. The compressive force is then released, and the resilient force exerted by the planar members then holds the container within the holes in a friction tight manner. The base of the clamp has an adhesive, such as velcro, so that the clamp can then be affixed to a support surface.

Thus, the container may be held in a rigid and stationary position while the cytology brush device is being rotated, or otherwise agitated, within the fin passageway. This permits a user to utilize two hands when rotating the brush, and also prevents the container from being accidently spilled.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention and its presently understood best mode for making and using the same will be described with additional specificity and detail through the use of the accompanying drawings in which.

In the drawing figures, like parts have been designated with like numerals throughout.

DETAILED DESCRIPTION OF THE PREFERRED EMBODIMENTS

Figure 1:
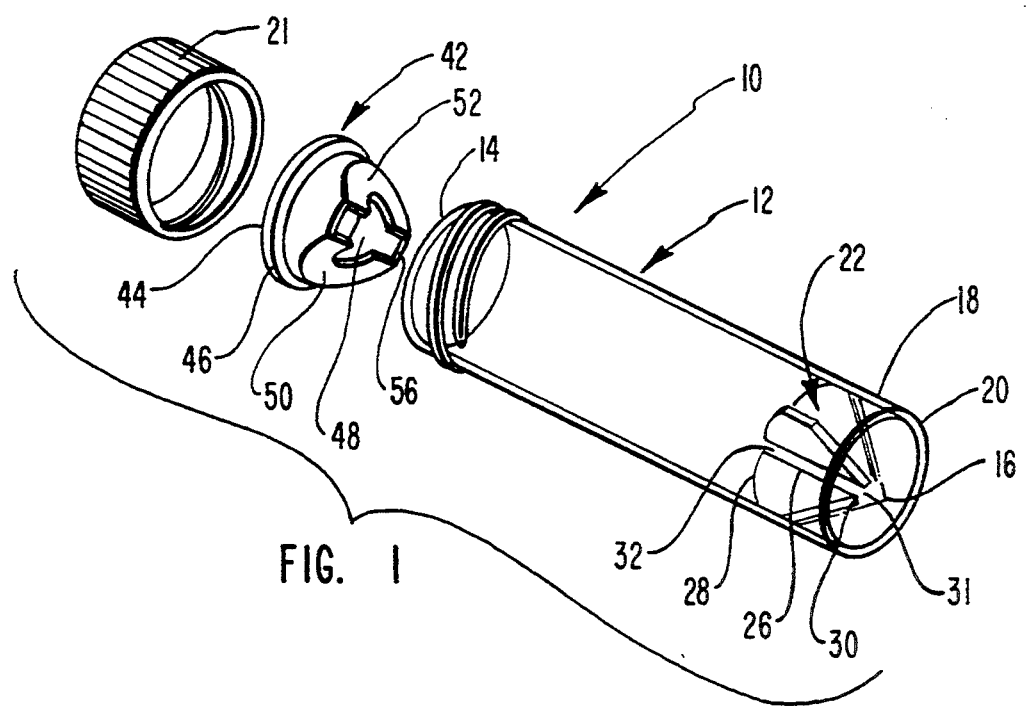
FIG. 1 is an exploded perspective view of one embodiment of the present invention.

Referring first to FIG. 1, one presently preferred embodiment of the present invention is illustrated and designated generally at 10. The collection apparatus 10 includes a cylindrical container 12 that has an open end 14 and a closed end 16. In a preferred embodiment, the interior of the container 12 at its closed end 16 is formed into a substantially conical shape. The outer periphery 18 of the container 12 extends to a point below the conically shaped closed end 16 thereby forming a flat base 20 upon which the container can stand. At the open end 14, a means for sealing the container 12 in a liquid tight manner, or a threaded cap 21, is threadably attached. However, as will be apparent to one skilled in the art, a variety of cap means may be utilized to seal the container 12 in a liquid tight manner.

Figure 2:
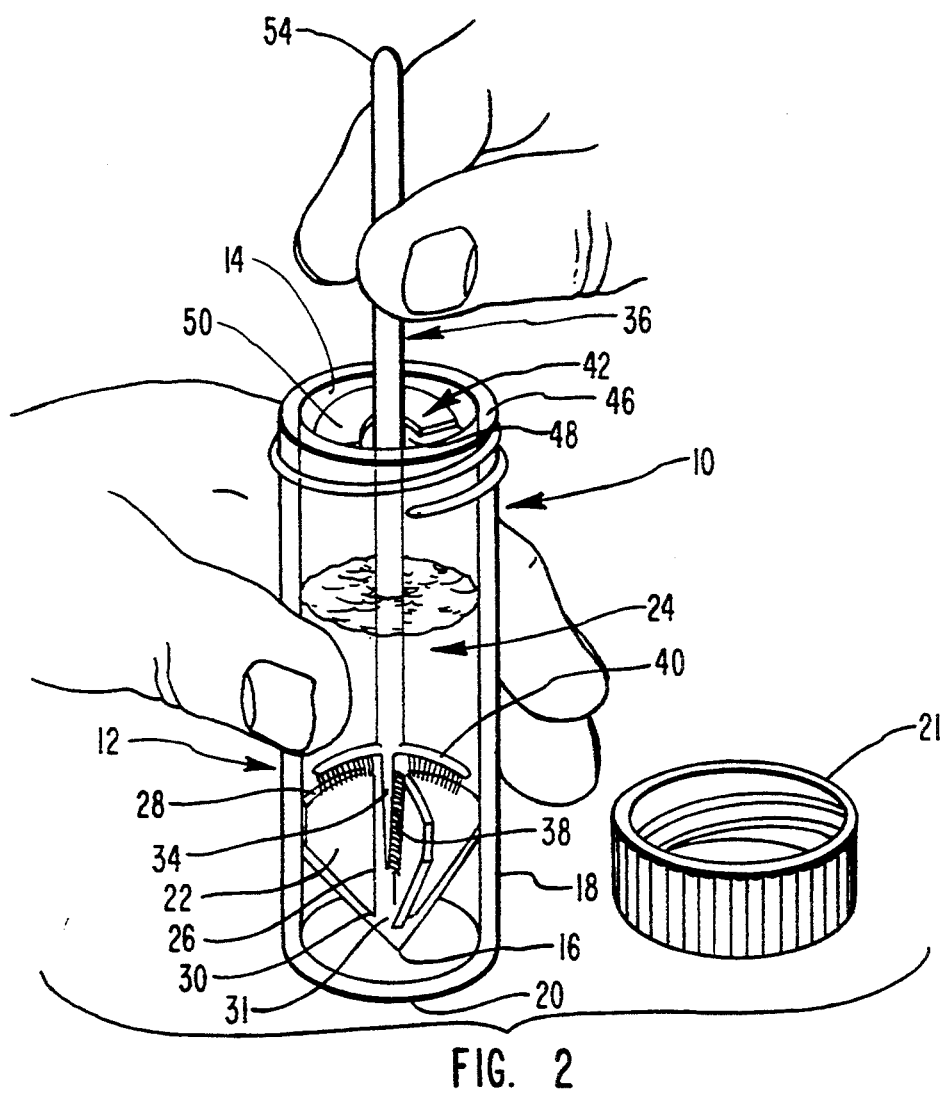
FIGS. 2 and 3 are perspective views of two types of cytology brush devices being disposed within the apparatus of the present invention and that are being agitated against the cell removal means.
Figure 4:
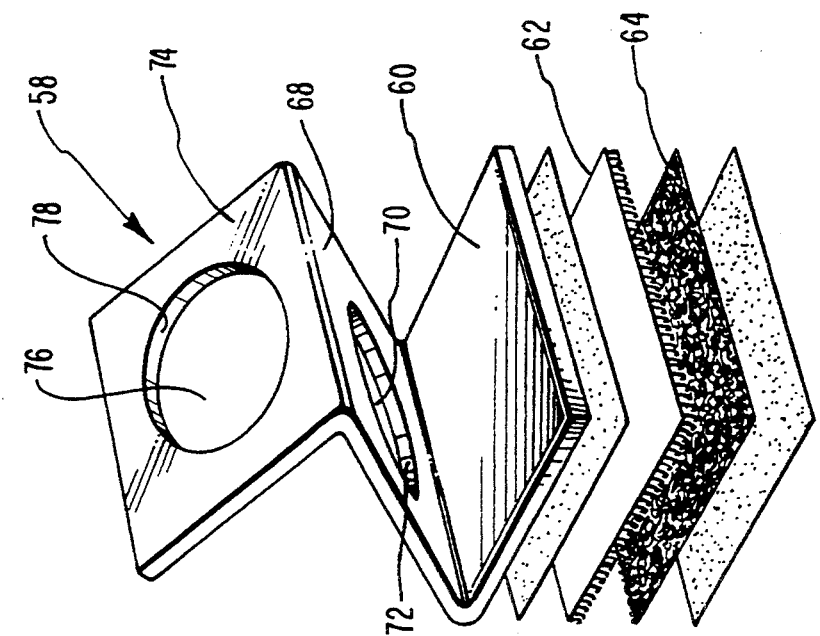
FIG. 4 is a perspective view of the clamping apparatus.
Figure 3:
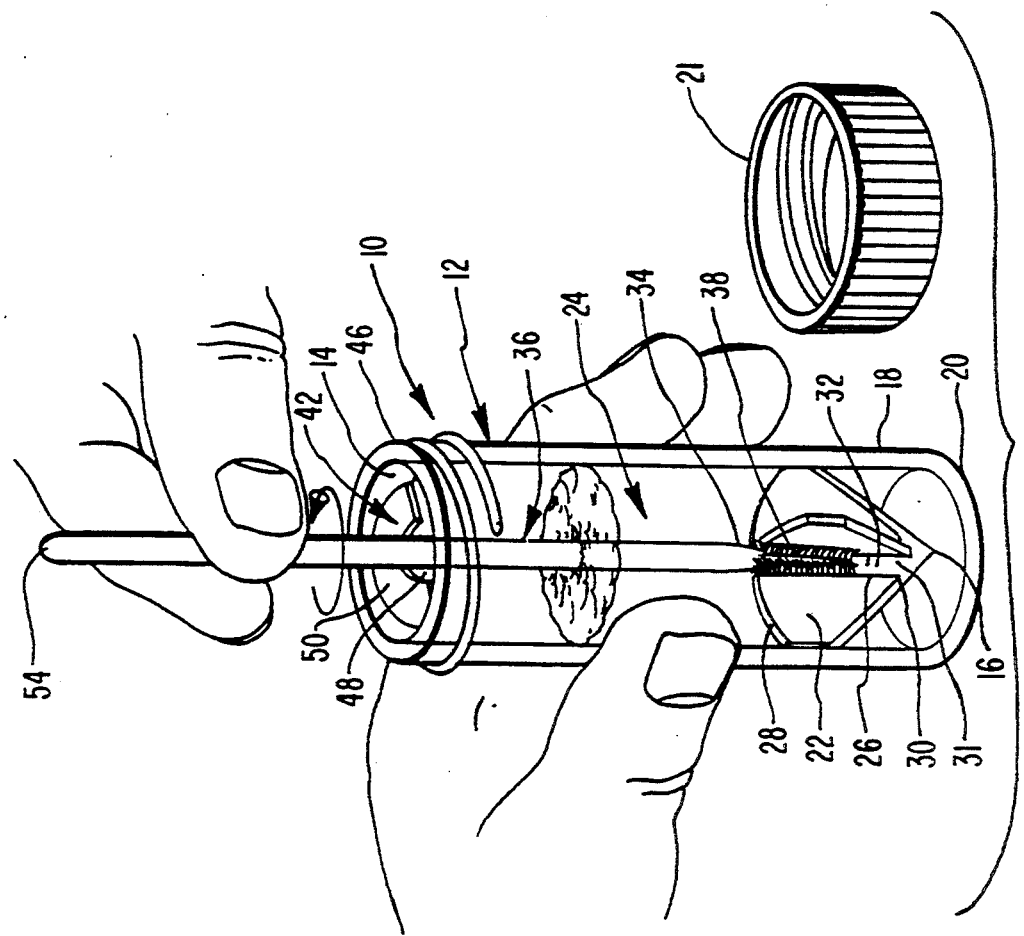

Disposed within the container 12 is a cell removal means, as for example a series of fins 22. As is illustrated in FIGS. 1 through 3, the fins 22 are affixed to the interior of the container 12 at a point where they are submerged within, for instance, a standard fixative solution 24 that is contained within the container 12. As will be apparent to one skilled in the art, a variety of other types of solutions that are capable of suspending a cell sample can also be used within the container 12. In the preferred embodiment, the fins 22 are located within the conical shaped portion of the closed end 16.

As can be seen in FIGS. 1 through 3, each of the fins 22 have a side lateral edge 26, a top lateral edge 28, and a bottom end 30. Each of the fins 22 are affixed to the interior walls of the container 12 and are preferably positioned so as to be substantially disposed within the conically shaped closed end 16. Preferably, each fin 22 is dimensioned such that the bottom end 30 does not completely extend to the extreme tip of the conically shaped closed end 16. In this way, there is a space 31 formed between the bottom end 30 of each fin 22 and the tip of the conically shaped closed end 16.

The fins 22 are oriented to project inwardly from the interior wall of the container 12 so as to meet in a spaced apart and opposed relationship with one another. Where the fins 22 meet in this spaced apart and opposed relationship, the side lateral edges 26 of the fins 22 act in conjunction to define a fin passageway 32. In the preferred embodiment, this fin passageway 32 is uniform in cross-section and has a central longitudinal axis that is concentric with the central longitudinal axis of the container 12. Further, the side lateral edge 26 of each fin is substantially flat and is parallel to the interior wall of the container 12.

Figure 7:
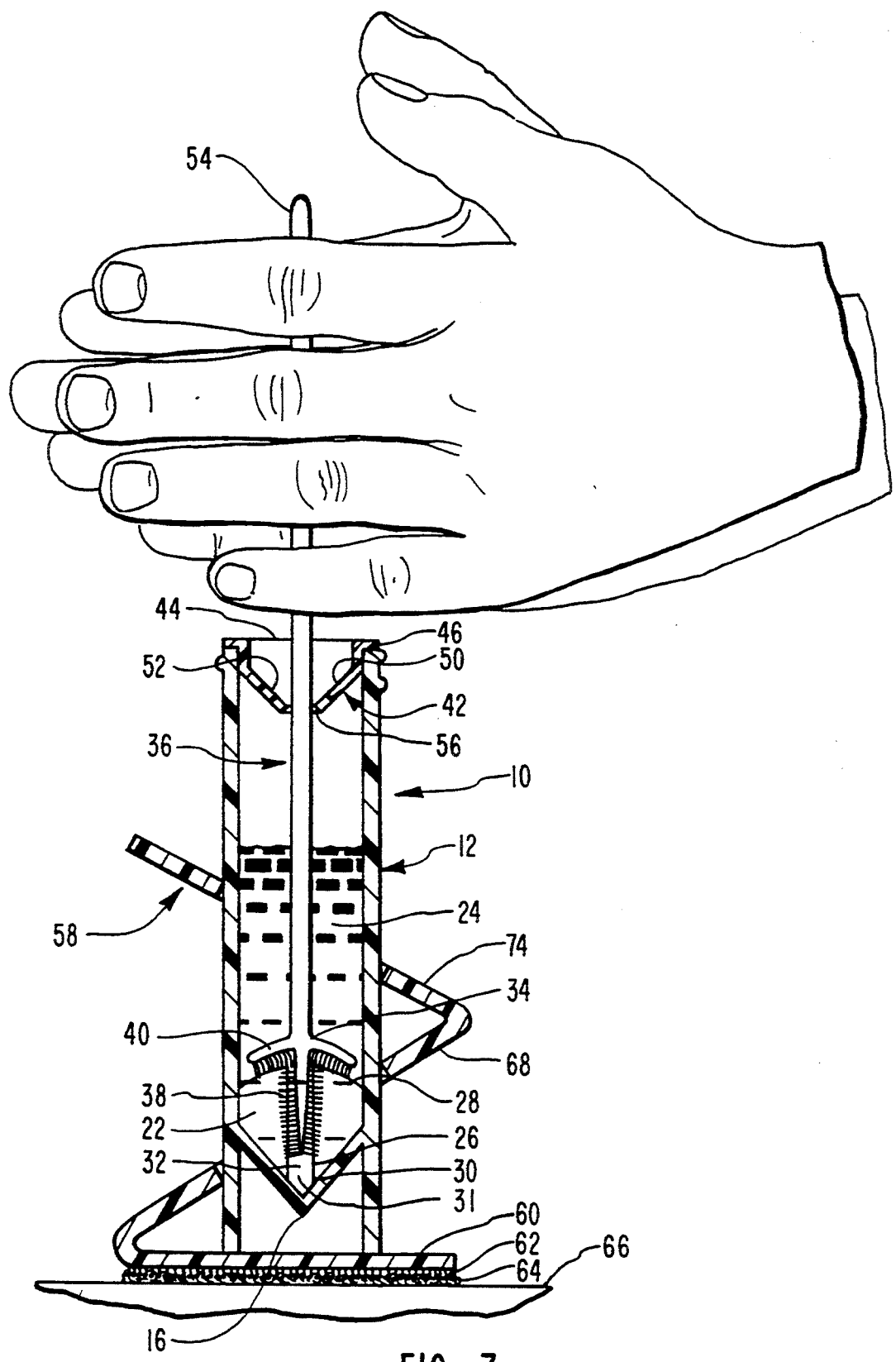
FIG. 7 is a cross-section taken along the line 7—7 of FIG. 6, illustrating a cytology brush device being inserted within the apparatus of the present invention and being rotated therein, and how the bristles are disposed and agitated within the fin passageway.

As is better shown in cross-section in FIGS. 3 and 7, the fin passageway 32 is able to receive the leading end 34, or bristled portion, of the cytology brush device 36. In operation, the bristles 38 of the cytology brush device 36 are agitated against each fin 22 by rotating the cytology brush within the container 12. In this way, the bristles 38 can be sufficiently agitated so that the cell samples will be dislodged from the bristles 38 and become suspended within the fixative solution 24. It will be appreciated that other fin arrangements could be oriented so that agitation of the brush bristles may occur in various other ways—such as, for instance, using an up and down motion.

As is best illustrated in FIGS. 2 and 7, in a preferred embodiment, the top lateral edge 28 of each fin 22 is slightly curved and substantially orthogonal to the side lateral edge 26 of each fin 22. In this way, the top lateral edge 28 can also act as an agitation surface to laterally extending bristled portions 40, which are also slightly curved in shape, that are present on certain cytology brush designs. A more complete description of a cytology brush 36 with such laterally extending bristled portions 40 is contained in U.S. Pat. No. 5,191,899, which is incorporated herein by reference. Thus, when a cytology brush of this type is rotated within the container 12, the laterally extending bristled portions 40 are agitated by the top lateral edge 28.

Thus, in the preferred embodiment the collection apparatus 10 can be used to collect cells from cytology brushes having different configurations. As discussed, the fins 22 provide an agitation surface for the cytology brush having laterally extending bristled portions 40. In addition, the fins 22 are also capable of providing an agitation surface for a standard, spiral shaped cytology brush, as is illustrated in FIG. 3.

With reference again to FIGS. 1 and 2, it is also illustrated how there is disposed within the open end 14 of the container 12 an alignment means, or cylindrically shaped insert 42. In the preferred embodiment, the insert is slidingly received within the open end 14 of the container 12 and is held there in a friction tight manner. The insert 42 has formed around the perimeter of its top end 44 an outwardly extending rim 46. The outward extending rim 46 is wider than the interior diameter of the container 12 and thus acts to prevent the insert 42 from being inserted within the container 12 beyond the point of the rim 46.

Referring now to FIG. 1, it is illustrated how the insert 42 has fashioned within it an alignment opening 48. In one preferred embodiment, the alignment opening 48 is fashioned as a circular hole with two laterally extending rectangular slits formed on both sides of the hole. It is through this alignment opening 48 that the cytology brush device 36 is inserted into the container 12. The alignment opening 48 is dimensioned such that both the spiral shaped cytology brush (FIG. 3), and the alternatively shaped cytology brush having laterally extending bristled portions (FIG. 2), may be accommodated in a free and unobstructed manner.

The alignment opening 48 is further positioned within the insert 42 so as to align the handle, or trailing end 54, of the cytology brush device 36 with the fin passageway 32. Thus, as is illustrated in FIGS. 3 and 7, as the cytology brush device 36 is being rotated within the container 12 so as to agitate its bristles 38 within the fin passageway 32, the alignment opening 48 acts to keep the trailing end 54 aligned with the fin passageway 32. Because the trailing end 54 is kept in this aligned position, the bristled, or leading end 34, of the cytology brush 36 tends to stay disposed within the fin passageway 32 as it is being rotated. This aids in the more efficient and complete agitation of the brush bristles 38 and thereby ensures a better cell sample.

With continued reference to FIG. 1, it is shown how there is positioned on each side of the alignment opening 48 a first guide surface 50 and a second guide surface 52. As is illustrated, in one preferred embodiment of the present invention, the first and second guide surfaces 50, 52 are each formed at equal angles with the interior walls of the container 12. In this embodiment, the guide surfaces 50, 52 are oriented so as to converge on the alignment opening 48 and thus taper towards the bottom end 56 of the insert 42. This tapered shape permits for the easy insertion of the leading end 34 of the cytology brush device 36 into the container. The tapered guide surfaces guide the leading end 34 into the alignment opening 48 and help prevent the bristles of the brush from being inadvertently rubbed or scraped against the inner edge of the open end 14 of the container 12 and thereby potentially losing a portion of the cell samples.

Figure 9:
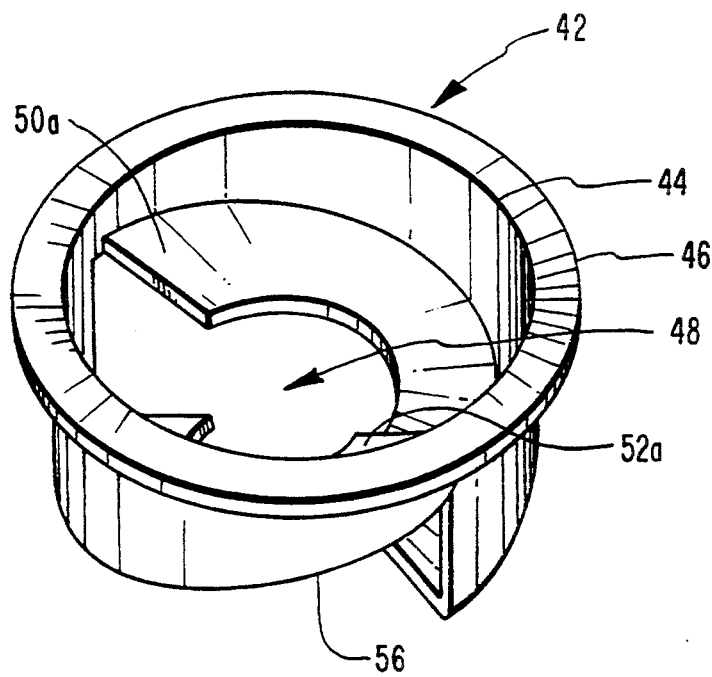
FIGS. 9 and 10 are perspective views of two different embodiments of the alignment inserts.
Figure 10:
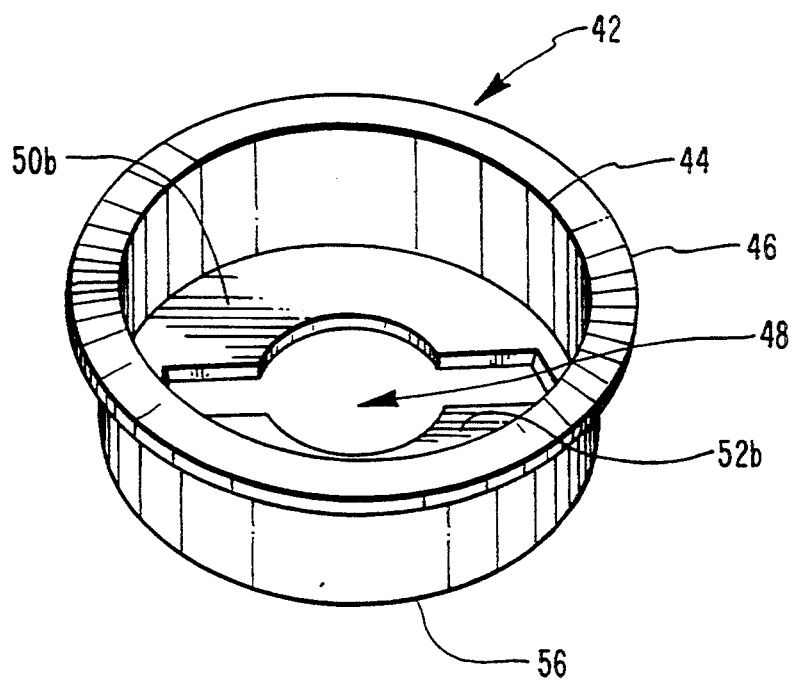

As can be seen in FIGS. 9 and 10, the present invention also contemplates using an insert 42 having guide surfaces 50, 52 that are oriented in different ways. Referring to FIG. 9, the first and the second guide surfaces $50^a$, $52^a$ each lie in separate planes that are angled from the lateral plane of the insert such that the guide surfaces $50^a$, $52^a$ form a screw-type incline towards the bottom end 56 of the insert 42. In FIG. 10, the first and the second guide surfaces $50^b$, $52^b$ lie in the same horizontal plane that is generally transverse to the longitudinal plane of the insert 42. Again, each of these embodiments will ease the insertion of the leading end 34 of the cytology brush device 36 and help prevent any inadvertent cell loss.

Referring now to FIGS. 4 through 8, another aspect of a preferred embodiment of the present invention is illustrated. Designated generally at 58 is a holding means, or Z-shaped clamp. The clamp 58 is preferably constructed from a resilient material, such as a polycarbonate. In the preferred embodiment the clamp 58 is formed as a single unitary structure. The clamp 58 has a base member 60 which has a means for securement, as for example a first adhesive 62 and a second and opposing adhesive 64, that is affixed to a support surface 66. In one preferred embodiment, the first and second adhesives 62, 64 are velcro strips, where one velcro strip is affixed to the base member 60 and the other opposing velcro strip is affixed to the support surface 66. In this way, the clamp 58 may be securely, but removably, affixed to the rigid support surface 66.

Formed at an angle with the base member is a first resilient gripping means, as for example a first planar surface 68. Formed within the first planar surface 68 is a first hole 70. The first hole 70 has a diameter that is only slightly greater than the outer diameter of the container 12 such that the container 12 can be slidably received within the first hole 70. Formed along the interior perimeter of the first hole 70 is a first inner edge 72.

Formed at an angle with the first planar surface 68 is a second resilient gripping means, as for example a second planar surface 74. Formed within the second planar surface 74 is a second hole 76. The second hole 76 has a diameter that, as with the first hole 70, is only slightly greater than the outer diameter of the container 12, again so as to allow the container 12 to be slidably received. Formed along the interior perimeter of the second hole 76 is a second inner edge 78.

Figure 5:
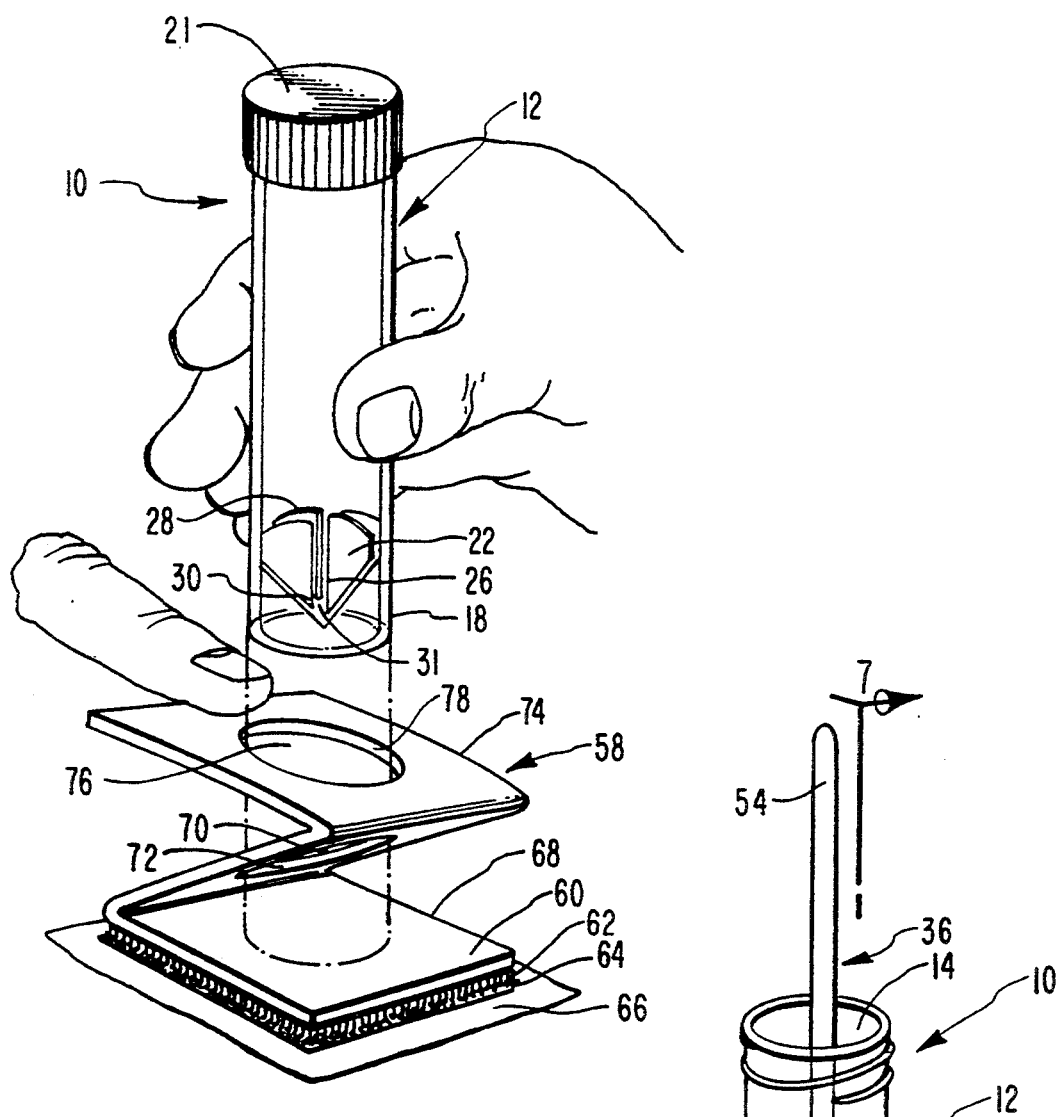
FIG. 5 is a perspective view of the cylindrical container being inserted into the clamp.
Figure 6:
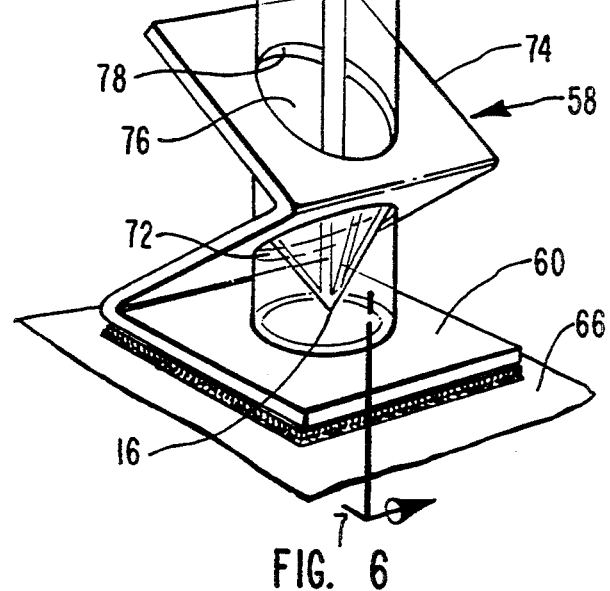
FIG. 6 is a perspective view of the cylindrical container being rigidly held within the clamp.

The operation of the clamp 58 is best illustrated in FIG. 5. There it is illustrated how the base member 60 is secured to the rigid support surface 66 by way of the first and second adhesives 62, 64. The second planar surface 74 is then pressed towards, or squeezed together with, the first planar surface 68 to a point where the second hole 76 is in substantial alignment with the first hole 70. At that point, the container 12 is inserted within the first and second holes 70, 76 and the squeezing or pressing pressure is released. At that time, the resilient spring force exerted by the first and second planar surfaces 68, 74 will urge a constant and friction-tight holding force on the container 12 with the first and second inner edges 72, 78. In this way, the container 12 is held in a rigid and secure manner.

As illustrated in FIG. 7, when the container 12 is securely held within in the clamp 58, the leading end 34 of the cytology brush device 36 may be rotated within the fin passageway 32 by rubbing the trailing end 54 of the device between two hands. This allows for a more efficient agitation of the brush bristles 38 and thus results in a more complete dislodging of the cell samples.

Figure 8:
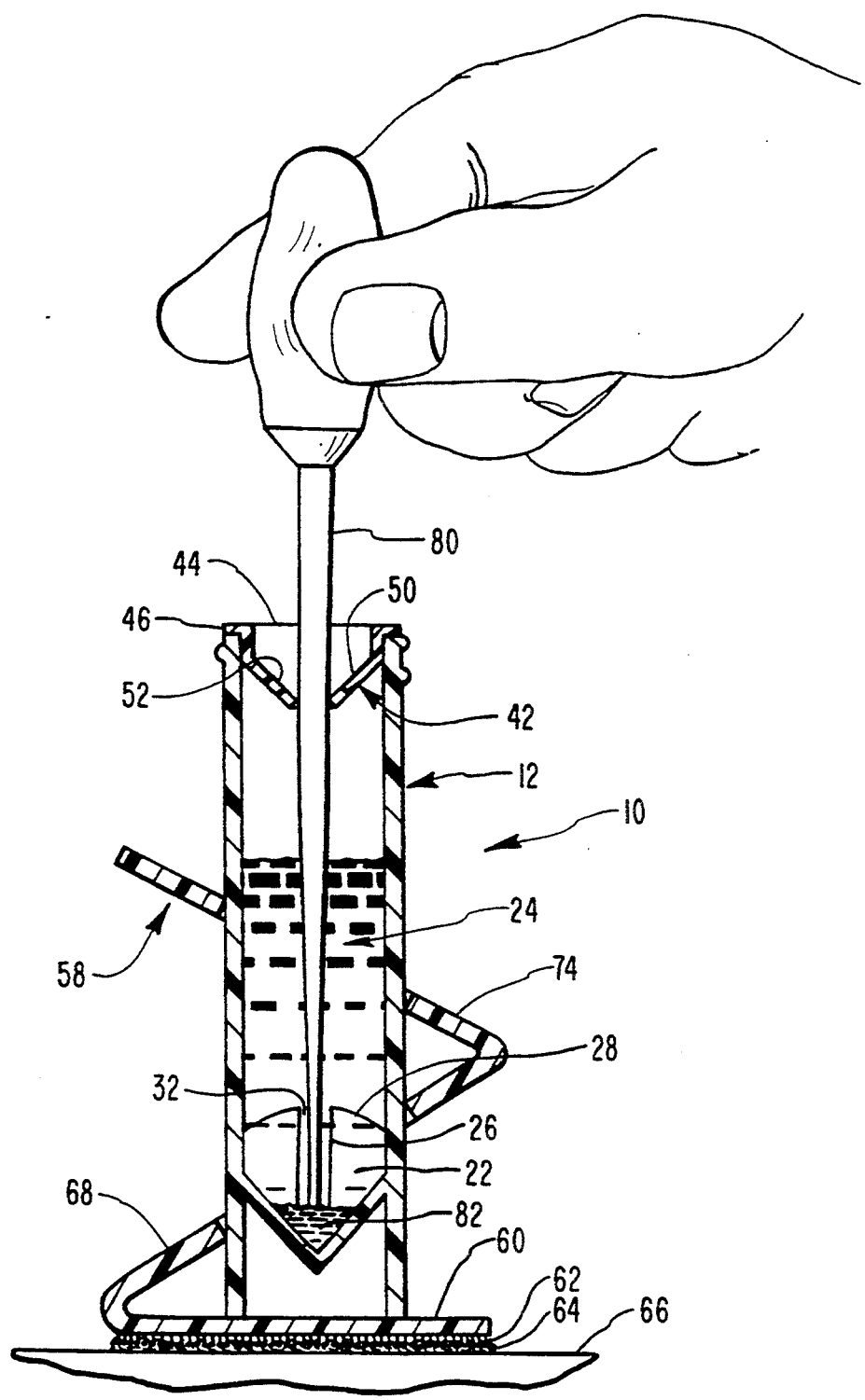
FIG. 8 is a cross-sectional view of how the cell sample can be removed from the apparatus of the present invention with a pipette type device.

After having agitated the bristles 38 of the cytology brush device 36 against the fins 22, the cell sample is dispersed within the fixative solution 24. At that time, the cytology brush 36 is removed from the container 12 and the threaded cap 21 is placed on the container so as to form a liquid tight seal. The container 12 can then be placed in a centrifuge and spun, so as to displace all of the cell sample to the spaced portion 31 located between the bottom ends 30 of the fins 22 and the extreme tip of the conically shaped closed end 16. As is illustrated in FIG. 8, the cell sample 82 can then be easily retrieved with a pipette type device 80, and placed onto a slide for later examination.

In the presently preferred embodiment of the cell collection apparatus, the preferred materials from which the apparatus is made is a clear, polycarbonate material that is inert with respect to various alcohol fixative solutions. It will be appreciated that a variety of other materials may also be used.

From the foregoing, it will be appreciated that a substantial advantage of the apparatus of the present invention is that cell samples contained on the bristles of a cytology brush device can be efficiently and effectively retrieved. The apparatus helps ensure that substantially all of the cells contained on the bristles are retrieved, and thus ensures that an accurate cell sample will be examined.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A collection apparatus for containing a solution that is used for the retrieval of cell samples from bristles of a cytology brush device having a body with a leading end and a trailing end, the collection apparatus comprising:
   (a) a container, adapted for containing a quantity of the solution, which has an open end and a closed end and wherein an interior portion of the container at the closed end is formed in a substantially conical shape;
   (b) a cell removal means, disposed within the container at a point so as to be submerged within the solution contained therein and above the closed end so as to provide a space therebelow for collection of the cell samples, for providing at least one essentially horizontal and at least one essentially vertical agitation surface against which the bristles of the cytology brush device can be agitated so as to dislodge the cell samples present on the bristles and thus suspend the cell samples within the solution; and
   (c) a cap means for sealing the container in a fluid tight manner after the cytology brush device is removed from within the container.

2. An apparatus as defined in claim 1, wherein the container is cylindrical in shape.

3. An apparatus as defined in claim 2 wherein the outer periphery of the cylindrically shaped container extends to a point below the conical shaped closed end so that the container is capable of standing in an upright and stable position on a flat and horizontal surface.

4. An apparatus as defined in claim 1, wherein the cell removal means comprises:

a plurality of fins affixed to an interior surface of the container, wherein each fin projects inwardly so that the fins meet in a spaced apart and opposed relationship and form a fin passageway therebetween, the fin passageway being capable of receiving the leading end of the cytology brush device such that the leading end of the cytology brush device is substantially centered and the bristles may be agitated against each said fin as the cytology brush device is rotated.

5. An apparatus as defined in claim 4, wherein the plurality of fins each have a top lateral edge, a side lateral edge, and a bottom end such that the side lateral edges act in combination to form the fin passageway between the inwardly projecting fins, and wherein the fin passageway is substantially uniform in cross section and has a central longitudinal axis that is concentric with the central longitudinal axis of the container, whereby the fin passageway is capable of receiving the leading end of the cytology brush device so that bristles can be agitated against both the top and the side lateral edges of each said fin as the cytology brush device is rotated.

6. An apparatus as defined in claim 5, wherein the top lateral edge of each said fin is slightly curved.

7. An apparatus as defined in claim 1, further comprising an alignment means, disposed at the open end of the container, for providing an alignment aperture adapted to hold the body of the cytology brush device in alignment with the cell removal means as the leading end of the cytology brush device is advanced into, and disposed within, the cell removal means, whereby the leading end of the cytology brush device tends to stay aligned with, and disposed within, the cell removal means as the cytology brush device is rotated and the bristles are agitated against the cell removal means.

8. An apparatus as defined in claim 7, wherein the alignment means comprises an insert, the insert having a cylindrical shape with a top and a bottom end where the outer perimeter of the top end is formed with an outwardly extending rim, the insert being slidingly received within the open end of the container and advanced therein to the point of said outwardly extending rim, the insert being then held within the container in a friction-tight manner, the insert further having an alignment opening formed therein and a first and a second guide surface formed on each side of the alignment opening, the alignment opening being shaped and dimensioned such that the leading end of the cytology brush device may be inserted through the alignment opening and into the container in a free and unobstructed manner.

9. An apparatus as defined in claim 8, wherein the alignment opening has a shape that is circular with two laterally extending rectangular slits.

10. An apparatus as defined in claim 9, wherein the first and the second guide surfaces generally lie in a single plane that is transverse to the longitudinal plane of the insert.

11. An apparatus as defined in claim 9, wherein the first and the second guide surfaces are each formed at equal angles with the interior of the insert such that the first and the second guide surfaces converge on said alignment opening thus tapering towards the bottom end of the insert.

12. An apparatus as defined in claim 9, wherein the first and the second guide surfaces lie in planes that are angled from the lateral plane of the insert such that each said guide surface forms a screw-type incline towards the bottom end of the insert.

13. An apparatus as defined in claim 1, further comprising a holding means for releasably securing the container to a support surface so that the container is held in a stationary and rigid position while the cytology brush device is inserted and rotated therein and the bristles are agitated against the cell removal means, the holding means comprising:
(i) a base member having releasable attachment means for securement to the support surface; and
(ii) first and second resilient gripping means mounted to the base member for receiving and holding the container, the first and the second resilient gripping means being together operative such that when the first and the second resilient gripping means are squeezed together the container can be slidably received by the first and the second resilient gripping means, and such that when the first and the second gripping means are released, the container is rigidly and non-slidably held by the first and the second gripping means.

14. An apparatus as defined in claim 13, wherein the first gripping means comprises a first planar surface having a first hole formed therein that has a diameter so as to be capable of slidably receiving said container, the first hole further having a first inner edge formed along the interior perimeter of said first hole, and wherein the second gripping means comprises a second planar surface having a second hole formed therein that has a diameter so as to be capable of slidably receiving said container, the second hole further having a second inner edge formed along the interior perimeter of said second hole, and wherein the first planar surface is formed at an angle with the second planar surface, the first and second planar surfaces further being resiliently moveable with respect to each other, whereby the first hole is aligned with the second hole by squeezing together the first planar surface and the second planar surface thus allowing the container to be slideably received within the first and second holes, the container thus being held in a friction tight manner by the first and the second said inner edges when the squeezing pressure is released.

15. An apparatus as defined in claim 13, wherein the releasable attachment means comprises a first adhesive affixed to the base member and a second and opposing adhesive affixed to the support surface, the first and the second adhesives being releasably attachable to one another.

16. A collection apparatus for containing a solution that is used for the retrieval of cell samples from bristles of a cytology brush device having a body with a leading end and a trailing end, the collection apparatus comprising:
(a) a container, adapted for containing a quantity of the solution, which has an open end and a dosed end and wherein the closed end is formed in a substantially conical shape;
(b) a cell removal means, disposed within the container at a point so as to be submerged within the solution contained therein and above the closed end so as to provide a space therebelow for collection of the cell samples, for providing an agitation surface against which the bristles of the cytology brush device can be agitated so as to dislodge the cell samples present on the bristles and thus suspend the cell samples within the solution, the cell removal means comprising:

a plurality of fins affixed to an interior surface of the container, wherein each fin projects inwardly so that the fins meet in a spaced apart and opposed relationship and form a fin passageway therebetween, and wherein the plurality of fins are affixed to the interior surface of the container within the conical shaped closed end, and wherein each said fin has a top lateral edge, a side lateral edge, and a bottom end such that the side lateral edges of each fin act in combination to form the fin passageway between the inwardly projecting fins, and wherein the fin passageway is substantially uniform in cross section and has a central longitudinal axis that is concentric with the central longitudinal axis of the container, whereby the fin passageway is capable of receiving the leading end of the cytology brush device so that the bristles can be agitated against the top and/or the side lateral edge of each said fin as the cytology brush device is rotated; and (c) a cap means for sealing the container in a fluid tight manner when the cytology brush device is not present within the container.

17. An apparatus as defined in claim 16, wherein the container is cylindrical in shape and wherein the outer periphery of the cylindrically shaped container extends to a point below the conical shaped closed end so that the container is capable of standing in an upright and stable position on a flat and horizontal surface.

18. An apparatus as defined in claim 17, further comprising an alignment means, disposed at the open end of the container, for providing an alignment aperture adapted to hold the body of the cytology brush device in alignment with the cell removal means as the leading end of the cytology brush device is advanced into, and disposed within, the cell removal means, whereby the leading end of the cytology brush device tends to stay aligned with, and disposed within, the cell removal means as the cytology brush device is rotated and the bristles are agitated against the cell removal means.

19. An apparatus as defined in claim 18, wherein the alignment means comprises an insert, the insert having a cylindrical shape with a top and a bottom end where the outer perimeter of the top end is formed with an outwardly extending rim, the insert being slidingly received within the open end of the container and advanced therein to the point of said outwardly extending rim, the insert being then held within the container in a friction-tight manner, the insert further having an alignment opening formed therein and a first and a second guide surface formed on each side of the alignment opening, the alignment opening being shaped and dimensioned such that the leading end of the cytology brush device may be inserted through the alignment opening and into the container in a free and unobstructed manner.

20. An apparatus as defined in claim 19, wherein the alignment opening has a shape that is circular with two laterally extending rectangular slits.

21. An apparatus as defined in claim 20, wherein the first and the second guide surfaces generally lie in a single plane that is transverse to the longitudinal plane of the insert.

22. An apparatus as defined in claim 20, wherein the first and the second guide surfaces are each formed at equal angles with the interior of the insert such that the first and the second guide surfaces converge on the said alignment opening thus tapering towards the bottom end of the insert.

23. An apparatus as defined in claim 20, wherein the first and the second guide surfaces lie in planes that are angled from the lateral plane of the insert such that each said guide surface forms a screw-type incline towards the bottom end of the insert.

24. An apparatus as defined in claim 20, further comprising a holding means for releasably securing the container to a support surface so that the container is held in a stationary and rigid position while the cytology brush device is inserted and rotated therein and the bristles are agitated against the cell removal means, the holding means comprising:

(i) a base member having releasable attachment means for securement to the support surface; and (ii) first and second resilient gripping means mounted to the base member for receiving and holding the container, the first and the second resilient gripping means being together operative such that when the first and the second resilient gripping means are squeezed together the container can be slidably received by the first and the second resilient gripping means, and such that when the first and the second gripping means are released, the container is rigidly and non-slidably held by the first and the second gripping means.

25. An apparatus as defined in claim 24, wherein the first gripping means comprises a first planar surface having a first hole formed therein that has a diameter so as to be capable of slidably receiving said container, the first hole further having a first inner edge formed along the interior perimeter of said first hole, and wherein the second gripping means comprises a second planar surface having a second hole formed therein that has a diameter so as to be capable of slidably receiving said container, the second hole further having a second inner edge formed along the interior perimeter of said second hole, and wherein the first planar surface is formed at an angle with the second planar surface, the first and second planar surfaces further being resiliently moveable with respect to each other, whereby the first hole is aligned with the second hole by squeezing together the first planar surface and the second planar surface thus allowing the container to be slideably received within the first and second holes, the container thus being held in a friction tight manner by the first and the second said inner edges when the squeezing pressure is released.

26. An apparatus as defined in claim 24, wherein the releasable attachment means comprises a first adhesive affixed to the base member and a second and opposing adhesive affixed to the support surface, the first and the second adhesives being releasably attachable to one another.

27. A collection apparatus for containing a solution that is used for the retrieval of cell samples from bristles of a cytology brush device having a body with a leading end and a trailing end, the collection apparatus comprising:

(a) a container, adapted for containing a quantity of the solution, which has an open end and a closed end wherein an interior portion of the container at the closed end is formed in a substantially conical shape;

(b) a cell removal means, disposed within the container at a point so as to be submerged within the solution contained therein, for providing an agitation surface against which the bristles of the cytology brush device can be agitated so as to dislodge the cell samples present on the bristles and thus suspend the cell samples within the solution, the cell removal means comprising:

a plurality of fins affixed to an interior surface of the container, wherein each fin projects inwardly so that the fins meet in a spaced apart and opposed relationship and form a fin passageway therebetween, wherein the plurality of fins are affixed to the interior surface of the container, and wherein each said fin has a top lateral edge and a side lateral edge, such that the side lateral edges of each fin act in combination to form the fin passageway between the inwardly projecting fins, and wherein the fin passageway is substantially uniform in cross section and has a central longitudinal axis that is concentric with the central longitudinal axis of the container, whereby the fin passageway is capable of receiving the leading end of the cytology brush device so that the bristles can be agitated against the top and the side lateral edge of each said fin as the cytology brush device is rotated;

(c) an alignment means, disposed at the open end of the container, for providing an alignment aperture adapted to hold the body of the cytology brush device in alignment with the fin passageway as the leading end of the cytology brush device is advanced into the fin passageway, whereby the leading end of the cytology brush device tends to stay aligned with, and disposed within, the fin passageway as the cytology brush device is rotated and the bristles are agitated against the fins; and (d) a cap means for sealing the container in a fluid tight manner after the cytology brush device is removed from within the container.

28. An apparatus as defined in claim 27, wherein the container is cylindrical in shape.

29. An apparatus as defined in claim 28, wherein the outer periphery of the cylindrically shaped container extends to a point below the conical shaped closed end so that the container is capable of standing in an upright and stable position on a flat and horizontal surface.

30. An apparatus as defined in claim 27, wherein the bottom end of each said fin is spaced apart from the closed end of the container.

31. An apparatus as defined in claim 30, wherein the alignment means comprises an insert, the insert having a cylindrical shape with a top and a bottom end where the outer perimeter of the top end is formed with an outwardly extending rim, the insert being slidingly received within the open end of the container and advanced therein to the point of said outwardly extending rim, the insert being then held within the container in a friction-tight manner, the insert further having an alignment opening formed therein and a first and a second guide surface formed on each side of the alignment opening, the alignment opening being shaped and dimensioned such that the leading end of the cytology brush device may be inserted through the alignment opening and into the container in a free and unobstructed manner.

32. An apparatus as defined in claim 31, wherein the alignment opening has a shape that is circular with two laterally extending rectangular slits.

33. An apparatus as defined in claim 32, wherein the first and the second guide surfaces generally lie in a single plane that is transverse to the longitudinal plane of the insert.

34. An apparatus as defined in claim 32, wherein the first and the second guide surfaces are each formed at equal angles with the interior of the insert such that the first and the second guide surfaces converge on the said alignment opening thus tapering towards the bottom end of the insert.

35. An apparatus as defined in claim 32, wherein the first and the second guide surfaces lie in planes that are angled from the lateral plane of the insert such that each said guide surface forms a screw-type incline towards the bottom end of the insert.

36. An apparatus as defined in claim 32, further comprising a holding means for releasably securing the container to a support surface so that the container is held in a stationary and rigid position while the cytology brush device is inserted and rotated therein and the bristles are agitated against the cell removal means, the holding means comprising:

(i) a base member having releasable attachment means for securement to the support surface; and (ii) first and second resilient gripping means mounted to the base member for receiving and holding the container, the first and the second resilient gripping means being together operative such that when the first and the second resilient gripping means are squeezed together the container can be slidably received by the first and the second resilient gripping means, and such that when the first and the second gripping means are released, the container is rigidly and non-slidably held by the first and the second gripping means.

37. An apparatus as defined in claim 36, wherein the first gripping means comprises a first planar surface having a first hole formed therein that has a diameter so as to be capable of slidably receiving said container, the first hole further having a first inner edge formed along the interior perimeter of said first hole, and wherein the second gripping means comprises a second planar surface having a second hole formed therein that has a diameter so as to be capable of slidably receiving said container, the second hole further having a second inner edge formed along the interior perimeter of said second hole, and wherein the first planar surface is formed at an angle with the second planar surface, the first and second planar surfaces further being resiliently moveable with respect to each other, whereby the first hole is aligned with the second hole by squeezing together the first planar surface and the second planar surface thus allowing the container to be slideably received within the first and second holes, the container thus being held in a friction tight manner by the first and the second said inner edges when the squeezing pressure is released.

38. An apparatus as defined in claim 36, wherein the releasable attachment means comprises a first adhesive affixed to the base member and a second and opposing adhesive affixed to the support surface, the first and the second adhesives being releasably attachable to one another.

39. A collection apparatus for containing a solution that is used for the retrieval of cell samples from bristles of a cytology brush device having a body with a leading end and a trailing end, the collection apparatus comprising:

(a) a container, adapted for containing a quantity of the solution, which has an open end and a closed end;

(b) a cell removal means, disposed within the container at a point so as to be submerged within the solution contained therein, for providing an agitation surface against which the bristles of the cytology brush device can be agitated so as to dislodge the cell samples present on the bristles and thus suspend the cell samples within the solution;

(c) a cap means for sealing the container in a fluid tight manner after the cytology brush device is removed from within the container; and (d) a holding means for releasably securing the container to a support surface so that the container is held in a stationary and rigid position while the cytology brush device is inserted and rotated therein and the bristles are agitated against the cell removal means, the holding means comprising:

(i) a base member having releasable attachment means for securement to the support surface; and (ii) first and second resilient gripping means mounted to the base member for receiving and holding the container, the first and the second resilient gripping means being together operative such that when the first and the second resilient gripping means are squeezed together the container can be slidably received by the first and the second resilient gripping means, and such that when the first and the second gripping means are released, the container is rigidly and non-slidably held by the first and the second gripping means and wherein the first gripping means comprises a first planar surface having a first hole formed therein that has a diameter to as to be capable of slidably receiving said container, the first hole further having a first inner edge formed along the interior perimeter of said first hole, and wherein the second gripping means comprises a second planar surface having a second hole formed therein that has a diameter so as to be capable of slidably receiving said container, the second hole further having a second inner edge formed along the interior perimeter of said second hole, and wherein the first planar surface is formed at an angle with the second planar surface, the first and second planar surfaces further being resiliently moveable with respect to each other, whereby the first hole is aligned with the second hole by squeezing together the first planar surface and the second planar surface thus allowing the container to be slideably received within the first and second holes, the container thus being held in a friction tight manner by the first and the second said inner edges when the squeezing pressure is released.

40. An apparatus as defined in claim 39, wherein the container is cylindrical in shape.

41. An apparatus as defined in claim 40, wherein an interior portion of the container at the closed end is formed in a substantially conical shape.

42. An apparatus as defined in claim 41 wherein the outer periphery of the cylindrically shaped container extends to a point below the conical shaped closed end so that the container is capable of standing in an upright and stable position on a flat and horizontal surface.

43. An apparatus as defined in claim 39, wherein the cell removal means comprises:

a plurality of fins affixed to an interior surface of the container, wherein each fin projects inwardly so that the fins meet in a spaced apart and opposed relationship and form a fin passageway therebetween, the fin passageway being capable of receiving the leading end of the cytology brush device such that the leading end of the cytology brush device is substantially centered and the bristles may be agitated against each said fin as the cytology brush is rotated.

44. An apparatus as defined in claim 43, wherein the plurality of fins each have a top lateral edge, a side lateral edge, and a bottom end such that the side lateral edges act in combination to form the fin passageway between the inwardly projecting fins, and wherein the fin passageway is substantially uniform in cross section and has a central longitudinal axis that is concentric with the central longitudinal axis of the container, whereby the fin passageway is capable of receiving the leading end of the cytology brush device so that the bristles can be agitated against the top and the side lateral edge of each said fin as the cytology brush device is rotated.

45. An apparatus as defined in claim 44, wherein the top lateral edge of each said fin is slightly curved.

46. An apparatus as defined in claim 45, wherein the bottom end of each said fin is spaced apart from the closed end of the container.

47. An apparatus as defined in claim 39, further comprising an alignment means, disposed at the open end of the container, for providing an alignment aperture adapted to hold the body of the cytology brush device in alignment with the cell removal means as the leading end of the cytology brush device is advanced into, and disposed within, the cell removal means, whereby the leading end of the cytology brush device tends to stay aligned with, and disposed within, the cell removal means as the cytology brush device is rotated and the bristles are agitated against the cell removal means.

48. An apparatus as defined in claim 47, wherein the alignment means comprises an insert, the insert having a cylindrical shape with a top and a bottom end where the outer perimeter of the top end is formed with an outwardly extending rim, the insert being slidingly received within the open end of the container and advanced therein to the point of said outwardly extending rim, the insert being then held within the container in a friction-tight manner, the insert further having an alignment opening formed therein and a first and a second guide surface formed on each side of the alignment opening, the alignment opening being shaped and dimensioned such that the leading end of the cytology brush device may be inserted through the alignment opening and into the container in a free and unobstructed manner.

49. An apparatus as defined in claim 48, wherein the alignment opening has a shape that is circular with two laterally extending rectangular slits.

50. An apparatus as defined in claim 49, wherein the first and the second guide surfaces generally lie in a single plane that is transverse to the longitudinal plane of the insert.

51. An apparatus as defined in claim 49, wherein the first and the second guide surfaces are each formed at equal angles with the interior of the insert such that the first and the second guide surfaces converge on the said alignment opening thus tapering towards the bottom end of the insert.

52. An apparatus as defined in claim 48, wherein the first and the second guide surfaces lie in planes that are angled from the lateral plane of the insert such that each said guide surface forms a screw-type incline towards the bottom end of the insert.

53. An apparatus as defined in claim 39, wherein the releasable attachment means comprises a first adhesive affixed to the base member and a second and opposing adhesive affixed to the support surface, the first and the second adhesives being releasably attachable to one another.

54. A collection apparatus for containing a solution that is used for the retrieval of cell samples from bristles of a cytology brush device having a body with a leading end and a trailing end, the collection apparatus comprising:

(a) a cylindrical container, adapted for containing a quantity of the solution, which has an open end and a closed end and wherein an interior portion of the container at the closed end is formed in a substantially conical shape, where the outer periphery of the cylindrical container extends below the conical shape portion of the closed end so that the container may stand on a flat horizontal surface;

(b) a plurality of fins affixed to an interior surface of the conical shaped closed end of the container at a point so as to be submerged within the solution contained therein, each said fin having a top lateral edge that is slightly curved, and a bottom end that is spaced from the closed end of the container, and a side lateral edge, wherein each fin projects inwardly so that the side lateral edges meet in a spaced apart and opposed relationship so as to form a fin passageway therebetween, the fin passageway being substantially uniform in cross section and having a central longitudinal axis that is concentric with the central axis of the cylindrical container, whereby the fin passageway is capable of receiving the leading end of the cytology brush device so that the bristles can be agitated against the top and the side lateral edge of each said fin as the cytology brush device is rotated;

(c) a cylindrically shaped insert having a top and a bottom end where the outer perimeter of the top end is formed with an outwardly extending rim, the insert being slidingly received within the open end of the container and advanced therein to the point of the outwardly extending rim, the insert being held within the container in a friction-tight manner, the insert further having an alignment opening formed therein that has a shape that is circular with two laterally extending rectangular slits, the insert further having a first and a second guide surface formed on each side of the alignment opening, the alignment opening further being so sized and positioned so as to align the body of the cytology brush device with the fin passageway as the cytology brush device is rotated and the bristles are agitated against the fins;

(d) a threaded cap that is threadably attachable to the closed end of the container, the cap being capable of sealing the container in a fluid tight manner after the cytology brush device is removed from within the container; and (e) a resilient Z-shaped clamp for releasably securing the container to a support surface so that the container is held in a stationary and rigid position while the cytology brush device is inserted and rotated therein and the bristles are agitated against the cell removal means, the clamp comprising:

(i) a base member having a first adhesive affixed to the base member and a second and opposing adhesive affixed to the support surface, the first and the second adhesives being releasably attachable to one another;

(ii) a first planar surface, formed at an angle with the base member, the first planar surface having a first hole formed therein that has a diameter so as to be capable of slidably receiving said container, the first hole further having a first inner edge formed along the interior perimeter of said first hole; and (iii) a second planar surface, formed at an angle with the first planar surface, the second planar surface having, a second hole formed therein that has a diameter so as to be capable of slidably receiving said container, the second hole further having a second inner edge formed along the interior perimeter of said second hole;

whereby the first and second planar surfaces are resiliently moveable with respect to each other such that the first hole is aligned with the second hole by squeezing together the first planar surface and the second planar surface thus allowing the container to be slideably received within the first and second holes, the container then being held in a friction tight manner by the first and the second said inner edges when the squeezing pressure is released.

* * * * *

UNITED STATES PATENT AND TRADEMARK OFFICE
CERTIFICATE OF CORRECTION

PATENT NO. : 5,422,273
DATED : June 6, 1995
INVENTOR(S) : DONALD L. GARRISON et al.

It is certified that error appears in the above-indentified patent and that said Letters Patent is hereby corrected as shown below:

```
    Title page, column 1, item [75], after "Ronald S. Merrell,
Provo," insert --A. Brent Strong, Sandy,--
    Column 1, line 26, "to tile" should be --to the--
    Column 2, line 11, "have:" should be --have--
    Column 10, lines 56-57, "dosed end" should be --closed end--
    Column 15, lines 30-31, "gripping- ,means" should be
--gripping means--
    Column 15, line 32, "to as" should be --so as--
    Column 18, line 34, delete ","
```

Signed and Sealed this

Fourteenth Day of November, 1995

Attest:

BRUCE LEHMAN

*Attesting Officer*     *Commissioner of Patents and Trademarks*